(12) United States Patent
Makovec et al.

(10) Patent No.: US 8,809,306 B2
(45) Date of Patent: Aug. 19, 2014

(54) COMBINATION ANDOLAST/GLUCOCORTICOIDS

(75) Inventors: Francesco Makovec, Lesmo (IT); Massimo Maria D'Amato, Monza (IT); Antonio Giordani, Pavia (IT); Lucio Claudio Rovati, Monza (IT)

(73) Assignee: Rottapharm S.p.A., Milan (IT)

( * ) Notice: Subject to any disclaimer, the term of this patent is extended or adjusted under 35 U.S.C. 154(b) by 1010 days.

(21) Appl. No.: 12/375,609

(22) PCT Filed: Jul. 31, 2006

(86) PCT No.: PCT/EP2006/064840
§ 371 (c)(1),
(2), (4) Date: Apr. 7, 2009

(87) PCT Pub. No.: WO2008/014814
PCT Pub. Date: Feb. 7, 2008

(65) Prior Publication Data
US 2009/0253664 A1    Oct. 8, 2009

(51) Int. Cl.
*A01N 45/00* (2006.01)
*A01N 43/64* (2006.01)
*A61K 31/56* (2006.01)
*A61K 31/41* (2006.01)

(52) U.S. Cl.
USPC ............................ 514/169; 514/171; 514/381

(58) Field of Classification Search
USPC .......................................... 514/169, 171, 381
See application file for complete search history.

(56) References Cited

U.S. PATENT DOCUMENTS

| 5,232,937 A | 8/1993 | Makovec et al. |
| 5,796,576 A | 8/1998 | Kim |
| 5,976,576 A * | 11/1999 | Makovec et al. ............... 424/489 |
| 2003/0125313 A1 * | 7/2003 | Gavin ........................... 514/179 |

FOREIGN PATENT DOCUMENTS

| EP | 1 634 595 A1 | 3/2006 |
| WO | 90/09989 | 9/1990 |
| WO | 2005/123071 A1 | 12/2005 |
| WO | 2005/123072 A1 | 12/2005 |

OTHER PUBLICATIONS

B.A. Spicer et al., "The effects of drugs on Sephadex-induced eosinophilia and lung hyper-responsiveness in the rat", Br. J. Pharmacol. (1990), pp. 821-828, vol. 101.
"Management of Chronic Obstructive Pulmonary Disease", Current Concepts, www.nejm.org, (Jun. 24, 2004), pp. 2689-2697, vol. 350.
A. I. Graul, "Respiratory drug development compendium", Allergic Rhinitis, Drugs of the Future, Dec. 2002, pp. 1181-1194, vol. 27, No. 12, XP009013244.
M. Cazzola, et al., "Effect of formoterol/budesonide combination on arterial blood gases in patients with acute exacerbation of COPD", Respiratory Medicine, Feb. 2006, pp. 212-217, vol. 100, No. 2, XP005243302.
E. Dompeling, et al., "Inhaled beclomethasone improves the course of asthma and COPD", European Respiratory Journal, Sep. 1992, pp. 945-952, vol. 5 No. 8, XP001078734.
Brown H M, "Response to prednisolone in COPD", The Lancet, Mar. 2001, p. 723, vol. 357, No. 9257, XP004801199.

* cited by examiner

*Primary Examiner* — Marcos Sznaidman
(74) *Attorney, Agent, or Firm* — Sughrue Mion, PLLC

(57) ABSTRACT

The invention relates to the combination of Andolast, a calcium-activated potassium channel opener and glucocorticoids for the treatment of patients suffering for airway diseases. Pharmaceutical compositions comprising Andoalst and glucocorticoids are also disclosed.

6 Claims, No Drawings

COMBINATION ANDOLAST/GLUCOCORTICOIDS

FIELD OF THE INVENTION

The present invention relates to the combination of andolast and glucocorticoids for the treatment of patients suffering from asthma, COPD or other respiratory diseases.

BACKGROUND OF THE INVENTION

Asthma is a chronic inflammatory disease of the respiratory system in which the airways narrow in response to different stimuli such as exposure to allergens, cold air, exercise and others. This narrowing causes symptoms such as wheezing, breathlessness, chest tightness and coughing, particularly at night or in the early morning.

Medication for asthma are used to reverse and prevent symptoms and airflow limitation and include controllers (or preventers) and relievers. The goal of treatment is to achieve "asthma control", which means to minimize day- and nighttime symptoms, activity limitation, airway narrowing and rescue bronchodilator use, and therefore reduce the risk of life-threatening exacerbations and long term morbidity.

Controllers are medications taken daily on a long-term basis that are useful in getting and keeping persistent asthma under control. Controllers include inhaled glucocorticoids, leukotriene modifiers, mast cell stabilizers, anticholinergics and long-acting $\beta_2$-agonists.

Relievers include short-acting, selective $\beta_2$-adrenoreceptor agonists, such as salbutamol and terbutaline, that act to relieve bronchoconstriction and its accompanying acute symptoms.

Chronic Obstructive Pulmonary Disease (COPD) is a disease state characterized by airflow limitation that is not fully reversible. The airflow limitation is usually both progressive and associated with an abnormal inflammatory response of the lungs to noxious particles, most often related to cigarette smoking.

The chronic airflow limitation characteristic of COPD is caused by a mixture of small airway disease (obstructive bronchiolitis) and parenchymal destruction (emphysema).

Chronic inflammation causes remodelling and narrowing of the small airways. Destruction of the lung parenchyma, also by inflammatory processes, leads to the loss of alveolar attachments to the small airways and decreases lung elastic recoil; in turn, these changes diminish the ability of the airways to remain open during expiration. The terms "emphysema" and "chronic bronchitis" are frequently used clinically and included in the definition of COPD. Emphysema, or destruction of the gas-exchanging surfaces of the lung (alveoli), describes one of several structural abnormalities present in patients with COPD.

As anticipated above, COPD is delineated by chronic inflammation throughout the airways, parenchyma, and pulmonary vasculature. The intensity as well as the cellular and molecular characteristics of the inflammation vary as the disease progresses. Over time, inflammation damages the lungs and leads to the pathologic changes characteristic of COPD (Sutherland et al.; N. Engl. J. Med. 2004 (350), 2689-97). In fact, COPD is characterised by an increase in neutrophils, macrophages, and T lymphocytes in various parts of the lungs. There may also be an increase of eosinophils in some patients, particularly during exacerbations.

Pharmacological therapy is used to prevent and control symptoms, reduce the frequency and severity of exacerbations, improve health status, and improve exercise tolerance. Therefore, treatment of COPD heavily depends on anti-inflammatory and bronchodilator drugs. However, none of the existing medications for COPD have been shown to modify the long-term decline in lung function that is the hallmark of this disease.

Andolast (CR 2039), chemically defined as N-4-(5-tetrazolyl)-phenyl-4-(5-tetrazolyl)-benzamide is a novel antiallergic and anti-inflammatory agent, belonging to a new class of calcium-activated potassium ($K^+$) channel openers.

Different sets of experiments have shown that Andolast relieves the different components of the airways inflammatory response. The compound decreases both the antibody-mediated and the cell-mediated inflammatory responses in atopic subjects. With regard to the former, Andolast has a potent inhibitory effect on IL-4 dependent IgE synthesis by human B lymphocytes from allergic donors: this effect leads to the decrease in allergen-triggered mast cells sensitisation and consequently to the inhibition of IgE-dependent mediator release.

With respect to cell-mediated processes, preliminary in-vivo data from atopic asthmatic patients indicated that Andolast induces an inhibitory effect on T lymphocytes ($Th_2$) production of the eosinophil recruiter cytokine IL-5.

The currently clinical pharmacology evidence indicates that Andolast administered by inhalation at doses ranging from 2 to 20 mg prevents in a dose-dependent fashion the airway hyperresponsiveness to specific as well as to non-specific bronchostimulation challenges such as AMP, exercise, UNDW (ultrasonically nebulized distilled water) and CAH (cold-dry air hyperventilation) in mild-moderate asthmatic patients. Moreover, Andolast completely prevents the early as well as the late airway response following specific antigen challenge.

DETAILED DESCRIPTION OF THE INVENTION

As specified above, the instant invention relates to a novel drug combination of andolast and glucocorticoids for the treatments of patients suffering from asthma, COPD or other respiratory diseases.

Andolast (CR 2039) chemically defined as N-4-(5-tetrazolyl)-phenyl-4-(5-tetrazolyl)-benzamide, has been mentioned in WO90/09989 as a potential agent for treatment of various conditions which can be attributed to hypersensitivity to allergens, such as bronchial asthma, allergic rhinitis and conjunctivitis and in EP1634595 as a drug to be used for the treatment of COPD.

Furthermore, suitable pharmaceutical formulations for the use of Andolast in the treatment of asthma have been described in U.S. Pat. No. 5,976,576.

Andolast is preferably used as di-sodium salt (and/or as solvate thereof).

Preferably, Andolast and the glucocorticoids are administered by inhalation at therapeutically effective dosages which, when combined, provide a rapid and sustained benefical effect for treating asthma, COPD and other airway disorders.

Definitions

Andolast can form salts and solvates which are also within the scope of this invention. Reference to Andolast is understood to include also salts and solvates thereof, unless otherwise indicated.

Glucocorticoids are a sub-class of corticosteroids, hormones that are produced in the adrenal cortex and are involved in a wide range of physiologic actions such as control of carbohydrate, fat and protein metabolism and are anti-inflammatory by preventing phospholipid release, decreasing eosinophil action and other mechanisms.

Synthetic glucocorticoids are used in the treatment of joint pain, dermatitis, hepatitis, lupus erythematosus, allergic reactions, asthma and other diseases for glucocorticoid replacement.

The preferred pharmacologically active glucocorticoids agents for use in accordance with the present invention include but are not limited to beclometasone dipropionate, fluticasone propionate, budesonide, mometasone furoate, zoticasone, dexamethasone and ciclesonide.

The term "combination" applied to active ingredients is used herein to define a single pharmaceutical composition (formulation) comprising both drugs of the invention (i.e., Andolast and glucocorticoid) or two separate pharmaceutical compositions (formulations), each comprising a single drug of the invention (i.e., Andolast or a glucocorticoid), to be administered conjointly.

Within the meaning of the present invention, the term "conjoint administration" is used to refer to administration of Andolast and a glucocorticoid simultaneously in one composition, or simultaneously in different composition, or sequentially.

For the sequential administration to be considered "conjoint", however Andolast and the glucocorticoid must be administered separately by a time interval that still permits to obtain rapid onset of action as well as good long-term efficacy for the treatment of asthma, COPD and other respiratory diseases. For example, Andolast and the glucocorticoid must be administered on the same day (e.g., each—once or twice daily), preferably within an hour of each other, and most preferably simultaneously.

The term "treating" is used herein to mean to relieve, alleviate, delay or prevent at least one symptom of disease in a subject. For example, in relation to patients with allergic asthma, the term "treat" may mean to improve quality of life of patients, associated with less exacerbations and greater reductions in the use of inhaled glucocorticoids.

As used herein the term "therapeutically effective" applied to dose or amount refers to that quantity of a compound or pharmaceutical composition that is sufficient to result in a desired activity upon administration to a human subject in need thereof. More specifically, the term "therapeutically effective" refers to that quantity of a compound or pharmaceutical composition that is sufficient to reduce or eliminate at least one symptom of asthma, COPD and other airway disorders.

The phrase "pharmaceutically acceptable", as used in connection with compositions of the invention, refers to molecular entities and other ingredients of such compositions that are physiologically tolerable and do not produce untoward reactions when administered to humans. Preferably, as used herein, the term "pharmaceutically acceptable" means approved by a regulatory agency of the Federal or a state government or listed in the U.S. Pharmacopeia or other generally recognized pharmacopeia for use in humans.

Within the meaning of the present invention, use is understood as meaning the oral inhalation, preferably administered in the form of an aerosol, the aerosol having a particle diameter preferably of between 0.1 and 10 microns and an average diameter preferably of between 1 and 3 microns.

Aerosol generation cab be performed by pressure jet atomizers, by propellant metered aerosols or by means of propellant-free conventional portable inhalers for dry powders as for example MIAT Monohaler®, Diskhaler®, Turbohaler® and Rotadisk®.

The administration forms, depending of the inhalation system used, may comprise the required excipients. In the case of powder inhalers water-soluble carriers, preferably lactose, sweeteners, preferably sodium saccharin, flavouring, preferably menthol or peppermint oil; in the case of metered aerosols propellants, emulsifiers, stabilizers, preservatives.

Andolast, preferably as di-sodium salt, is usually administered in a dose-range from 2 to 24 mg, advantageously from 8 to 16 mg, from one to three times daily.

The glucocorticoid, depending on the active compound, is usually administered in a dosage of 0.05 to 2 mg per day. In the case of the budenoside the daily preferred dosage may be in the range of from 0.1 to 1 mg daily.

The invention further provides pharmaceutical preparations for treating asthma, COPD and other airway disorders, which preparations comprise as active compounds, Andolast and a glucocorticoid.

The invention also provides a pharmaceutical medicament comprising one or more containers containing one or more of the ingredients of the formulations of the invention. In a related embodiment, the present invention provides a kit for the preparation of the pharmaceutical compositions of the invention, said kit comprising Andolast in a first container, and a glucocorticoid in a second container, and, optionally, instructions for admixing the two drugs and/or for administration of the compositions. Each container of the kit may also optionally include one or more physiologically acceptable carriers and/or excipients and/or auxiliary substances. Associated with such container(s) can be a notice in the form prescribed by governmental agency regulating the manufacture, use or sale pharmaceuticals products, which notice reflects approval by the agency of manufacture, use or sale for human administration.

According to the methods of the present invention, the pharmaceutical compositions described herein are administered to patient at therapeutically effective doses, preferably, with minimal toxicity. Preferably, Andoalst and the glucocorticoid are each used at a dosage which, when combined, provide an enhanced effect, most preferably, an effect not observed upon administration of each agent alone.

The invention is illustrated further by the following specific pharmaceutical compositions which should not, however, be considered in any way limiting of the invention.

EXAMPLE 1

| | |
|---|---|
| Andolast sodium salt | 8.00 mg |
| Budesonide | 0.20 mg |
| Lactose | 7.00 mg |
| Menthol | 0.30 mg |
| Sodium Saccharin | 0.50 mg |
| Total | 16.00 mg |

EXAMPLE 2

| | |
|---|---|
| Andolast sodium salt | 16.00 mg |
| Budesonide | 0.20 mg |
| Lactose | 6.80 mg |
| Menthol | 0.40 mg |
| Sodium Saccharin | 0.60 mg |
| Total | 24.00 mg |

EXAMPLE 3

| Andolast sodium salt | 8.00 mg |
| --- | --- |
| Fluticasone propionate | 0.25 mg |
| Lactose | 7.00 mg |
| Menthol | 0.30 mg |
| Sodium Saccharin | 0.45 mg |
| Total | 16.00 mg |

EXAMPLE 4

| Andolast sodium salt | 8.00 mg |
| --- | --- |
| Beclometasone dipropionate | 0.25 mg |
| Lactose | 7.00 mg |
| Menthol | 0.30 mg |
| Sodium Saccharin | 0.45 mg |
| Total | 16.00 mg |

The efficacy of Andolast, glucocorticoids and their combinations was determined in preclinical studies using small animal models (e.g., rats) in which both the components of the invention have been found to be therapeutically effective.

The drug combination of the invention is not only highly effective at relatively low doses, but also posses low toxicity and produces few side effects.

Preclinical Studies

The combination treatment of Andolast with prednisolone, taken as the representative of glucocorticoids, has been studied in comparison with the monotherapy of the same drugs in one model of lung eosinophilia and hyperreactivity in rats, mimicking conditions of human asthma.

Effect on Sephadex-induced Eosinophilia and Lung Hyperresponsiveness in Rats

Lung eosinophilia and hyperreactivity are characteristic of chronic asthma. Eosinophilia and hypereactivity in the lungs of rats was induced by intravenous injection of Sephadex particles, according to the method of Spicer et al. (Brit. J. Pharmacol. (1990), 101, 821-828). A single injection of Sephadex G100 induces an increase in number of eosinophils in the bronchoalveolar lavage (BAL) fluids of the rats and moreover the animals become hyperresponsive to the bronchoconstriction induced by acetylcholine (Ach).

In this context, we examined the effect of Andolast, prednisolone and one combination of these two drugs.

On day 0 the animals were injected i.v. (5 ml/kg) with 1.5 mg/ml suspension of Sephadex G100.

The same day rats received the drugs 1 hour before and 3 hours after the injection of G100. The drug treatment was followed once a day from day 1 to day 3 and 1 hour before measurement of airway responsiveness to Ach on day 4.

Andolast di-sodium salt was given i.m. 3 ml/kg dissolved in saline, prednisolone was given orally 5 ml/kg suspended in 0.5% methylcellulose. Bronchoconstriction was induced by Ach; it was administered i.v. (1 ml/kg) at 5 min intervals and was increased from 0.03, 0.1, 0.3 to 3 mg/kg.

Bronchoconstriction was determined as $ED_{50}$ (mg/kg), i.e. the dose of Ach which produced 50% response calculated from the regression line of the dose-response curve. The results obtained are shown in Table 1.

TABLE 1

Protective effect of Andolast, prednisolone and their combination treatment on airway hyperresponsiveness induced by Sephadex G100 particles.

| Treatment group | Doses (mg/kg) | Ach $ED_{50}$ (mg/kg) | Protective[1] Effect (%) |
| --- | --- | --- | --- |
| Control (C) | — | 0.32 | — |
| G-100 (G) | — | 0.14 | — |
| G-100 (T) | Andolast (3) | 0.20 | 33.3 |
| G-100 (T) | Prednisolone (1) | 0.16 | 11.1 |
| G-100 (T) | Prednisolone (10) | 0.30 | 88.8 |
| G-100 (T) | Andolast (3) + Prednisolone (1) | 0.28 | 77.7 |

[1]The protective effect (%) was calculate by the formula:
$$\frac{(T-G)}{(C-G)} \times 100$$

The calculated protective effects of Andolast (3 mg/kg) and prednisolone (1 mg/kg) given alone were 33.3% and 11.1%, respectively, whereas the prednisolone (10 mg/kg) produced an almost complete protection (88.8%). The combination treatment at the given doses produced a 77.7% protection.

Therefore the combination treatment produced a synergistic increase in efficacy for both drugs, as for example Andolast (3 mg/kg) was able to produce an increase of efficacy of prednisolone (1 mg/kg) of about 7 times.

The counts of eosinophils in the BAL fluid were significantly increased in the Sephadex-injected (control) rats ($2.6 \times 10^6$) as compared to those in the normal rats (about $1 \times 10^4$).

Prednisolone (10 mg/kg) totally suppressed the eosinophilia in the BAL fluids, whereas prednisolone (1 mg/kg) was poorly effective ($2 \times 10^6$).

Andolast (3 mg/kg) slightly inhibited lung eosinophilia ($1.75 \times 10^6$), whereas the combination treatment produced about a 80% protection ($0.52 \times 10^6$).

Therefore also in the case of eosinophilia in the BAL fluids the combination treatment produced a synergistic protective effect for both drugs.

Clinical Studies

Safety and Efficacy of Andolast as Add-on to Glucocorticoids in the Relief of Allergic Asthma To assess the safety and efficacy of Andolast in adult patients with persistent asthma treated with glucocorticoids, we propose to conduct a multicenter, randomized, placebo-controlled, double-blind, dose-response, parallel-group trial of inhaled Andolast as add-on treatment to low-dose of inhaled budesonide to investigate the efficacy and safety of this drug combination.

The synopsis below describes a possible study design.

Only patients with mild to moderate persistent allergic asthma ($FEV_1 \leq 80\%$ of predicted value) will be enrolled in this study.

To participate patients must have received during a run-in period of 4 weeks an adequate dose of metered-dose inhaled glucocorticoid (budesonide 400 mcg b.i.d.) to reach an adequate asthma control.

Eligible patients, i.e. patients that have obtained asthma control as shown by a significant improvement in $FEV_1$ and symptoms, will be randomised, stratified according to asthma severity in four groups of treatment, as follows:

Placebo (budesonide 100 mcg b.i.d.)
Andolast (budesonide 100 mcg+Andolast 8 mg b.i.d.)
Andolast (budesonide 100 mcg+Andolast 16 mg b.i.d.)
Andolast (budesonide 100 mcg+Andolast 24 mg b.i.d.)

Patients will record lung function and day time and nigh time asthma symptoms throughout the study.

The primary objective of the study is to assess the effect of treatment on airway obstruction ($FEV_1$, PEF and FVC), "rescue" medication use, day and night-time asthma symptoms score, activity limitation, number of exacerbations, time to first exacerbation of asthma, drop-out to severe asthma exacerbation.

While the invention has been depicted and described with reference to exemplary embodiments, such reference does not imply a limitation on the invention, and no such limitation is to be inferred. The invention is capable of considerable modification, alteration, and equivalents in form and function, as will be apparent to those of ordinary skill in the pertinent art having the benefit of this disclosure. Consequently, the invention is intended to be limited only by the spirit and scope of the appended claims, giving full cognizance to equivalence in all respects.

The invention claimed is:

1. A method of treating asthma, COPD, or a respiratory disease comprising administering to a patient in need of such treatment a therapeutically effective amount of (i) Andolast di-sodium salt and/or a solvate thereof and (ii) a second therapeutically effective amount of budesonide, wherein Andolast di-sodium salt and/or solvate thereof and budesonide are in a ratio by weight of between 8 and 320 with reference to the Andolast di-sodium salt.

2. The method of claim 1 in which the respiratory disease is selected from the group consisting of bronchitis, obstructive bronchitis, allergic bronchitis, pulmonary fibrosis, pneumonia, emphysema.

3. The method of claim 1 in which andolast di-sodium salt and budesonide are administered conjointly.

4. The method of claim 1 in which andolast di-sodium salt and budesonide are administered sequentially.

5. The method of claim 1 in which andolast di-sodium salt and budesonide are administered simultaneously, sequentially or separately by oral inhalation.

6. The method of claim 1 in which andolast di-sodium salt is used as add-on to budesonide in long-term maintenance treatment of asthma, COPD and other respiratory diseases.

* * * * *